(12) United States Patent
Dollings

(10) Patent No.: US 6,451,767 B1
(45) Date of Patent: Sep. 17, 2002

(54) BENZYLMALTOTRIOSIDES AS INHIBITORS OF SMOOTH MUSCLE CELL PROLIFERATION

(75) Inventor: Paul J. Dollings, Newtown, PA (US)

(73) Assignee: Wyeth, Madison, NJ (US)

( * ) Notice: Subject to any disclaimer, the term of this patent is extended or adjusted under 35 U.S.C. 154(b) by 0 days.

(21) Appl. No.: 09/903,078

(22) Filed: Jul. 11, 2001

Related U.S. Application Data

(62) Division of application No. 09/444,733, filed on Nov. 22, 1999, now Pat. No. 6,291,434.
(60) Provisional application No. 60/126,441, filed on Nov. 24, 1998.

(51) Int. Cl.[7] ............................................. A61K 31/702
(52) U.S. Cl. ............................. 514/25; 514/56; 514/61
(58) Field of Search ............................. 514/25, 56, 61; 536/4.1, 17.9

(56) References Cited

U.S. PATENT DOCUMENTS

| | | |
|---|---|---|
| 2,752,334 A | 6/1956 | Walton |
| 4,431,637 A | 2/1984 | Upeslacis et al. |
| 5,019,562 A | 5/1991 | Folkman et al. |
| 5,037,973 A | 8/1991 | Meinetsberger |
| 5,296,588 A | 3/1994 | Au et al. |
| 5,336,765 A | 8/1994 | Au et al. |
| 5,464,827 A | 11/1995 | Soll |
| 5,498,775 A | 3/1996 | Novak et al. |
| 5,739,115 A | 4/1998 | Fugedi et al. |

FOREIGN PATENT DOCUMENTS

| | | |
|---|---|---|
| EP | 0312086 | 4/1989 |
| EP | 0312087 | 4/1989 |
| EP | 0454220 | 10/1991 |
| EP | 0551675 | 7/1993 |
| WO | 9006755 | 6/1990 |
| WO | 9309790 | 5/1993 |
| WO | 9614324 | 5/1996 |
| WO | 9614325 | 5/1996 |

OTHER PUBLICATIONS

Zehavi, Carbohyd. Res., 1986, 151, 371.
Reilly et al., Drug Development Research, 1993, 29, 137.
Klein et al., Liebigs Ann. Chem., 1987, 485–489.
Durette et al., Carbohydrate Research, 1978, 67, 484–490.
Bertho, Liebigs Ann. Chem., 1949, 562, 229–239.
Kopper et al., Carbohydrate Research, 1989, 193, 296–302.
Sato et al., Tetrahedron Lett., 1988, 29 (3), 4097–100.
McAuliffe et al., Aust. J. Chem., 1997, 50 (3), 197–202.
Zehavi et al., Carbohydrate Research, 1983, 124, 23–34.
Zehavi et al., Carbohydrate Research, 1992, 228, 255–263.
Connors et al., Herba Polonica, 1998, 44, 33–38.
Morales et al., Angew. Chem. Int. Ed., 1988, 37 (5), 654–657.
Ferro, V. et al "Synthesis of 2'–and 2" –O–acylated maltotriosides as potential fluorescence–quenched substrates for alpha–amylose" J. Chem., Soc., Perkins, Trans., vol. 15, pp. 2169–3276.
Koto, S. et al, "Dehydrative glycosylation using heptabenzyl derivatives of glucobioses and lactose", vol. 65, No. 12, pp. 3257–3274.
Hirooka, M., et al "Dehydrative glycosylatin by diethylaminosulfur trifluoride (DAST)", vol 71 pp. 2893–2902.

*Primary Examiner*—James O. Wilson
*Assistant Examiner*—Leigh Maier
(74) *Attorney, Agent, or Firm*—Michael Nagy

(57) ABSTRACT

This invention provides smooth muscle cell proliferation inhibitors of formula I having the structure

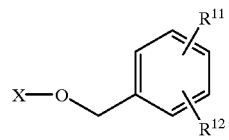

wherein X is

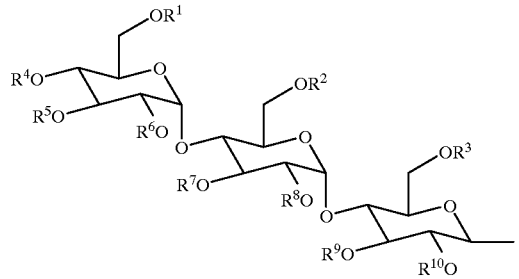

$R^1$, $R^2$, $R^3$, $R^4$, $R^5$, $R^6$, $R^7$, $R^8$, $R^9$ and $R^{10}$, are each, independently, hydrogen, acyl of 2–7 carbon atoms, perfluoroacyl of 2–10 carbon atoms, alkyl of 1–6 carbon atoms, perfluoroalkyl of 1–6 carbon atoms, benzoyl, benzyl or —$SO_3M$;

M is hydrogen, lithium, sodium, potassium or ammonium;

$R^{11}$ is hydrogen, alkyl of 1–6 carbon atoms, perfluoroalkyl of 1–6 carbon atoms, halogen, nitrile, nitro, or alkoxy of 1–6 carbon atoms;

$R^{12}$ is hydrogen, nitro, amino, acylamino of 2–7 carbon atoms, perfluoroacylamino of 2–7 carbon atoms, alkylamino of 1–6 carbon atoms, perfluoroalkylamino of 1–6 carbon atoms, dialklylamino where each alkyl chain is independently 1–6 carbon atoms, perfluorodialklylamino where each alkyl chain is independently 1–6 carbon atoms alkylsulfonylamino of 1–6 carbon atoms, perfluoroalkylsulfonylamino of 1–6 carbon atoms, arylsulfonylamino of 6–10 carbon atoms or arylsulfonylamino substituted with halo of 6–10 carbon atoms;

or a pharmaceutically acceptable salt thereof.

4 Claims, No Drawings

BENZYLMALTOTRIOSIDES AS INHIBITORS OF SMOOTH MUSCLE CELL PROLIFERATION

This is a divisional of application(s) Ser. No. 09/444,733 filed on Nov. 22, 1999, now U.S. Pat. No. 6,291,434, the entire disclosure of which is hereby incorporated by reference.

This application claims the benefit of U.S. Provisional Application No. 60/126,441, which was converted from U.S. patent application Ser. No. 09/198,805, filed Nov. 24, 1998, pursuant to a petition filed under 37 C.F.R. 1.53(c)(2)(i).

BACKGROUND OF THE INVENTION

This invention relates to the use of substituted benzylmaltotriosides as smooth muscle cell proliferation inhibitors and as therapeutic compositions for treating diseases and conditions which are characterized by excessive smooth muscle proliferation such as restenosis.

All forms of vascular reconstruction such as angioplasty and vein bypass procedures effect a response to injury that ultimately leads to smooth muscle cell (SMC) proliferation and subsequently, deposition of profuse amounts of extracellular matrix (Clowes, A. W.; Reidy, M. A. *J. Vasc. Surg* 1991, 13, 885). These events are also central processes in the pathogenesis of atherosclerosis (Raines E. W.; Ross R. *Br. Heart J.* 1993, 69 (Supplement), S. 30) as well as transplant arteriosclerosis (Isik, F. F.; McDonald, T. O.; Ferguson, M.; Yamanaka, E.; Gordon *Am. J. Pathol.* 1992, 141, 1139). In the case of restenosis following angioplasty, clinically relevant solutions for controlling SMC proliferation through pharmacological intervention have remained elusive to date (Herrman, J. P. R.; Hermans, W. R. M.; Vos, J.; Serruys P. W. *Drugs* 1993, 4, 18 and 249). Any successful approach to selective SMC proliferation inhibition must not interfere with endothelial cell repair or the normal proliferation and function of other cells (Weissberg, P. L.; Grainger, D. J.; Shanahan C. M.; Metcalfe, J. C. *Cardiovascular Res.* 1993, 27, 1191).

The glycosaminoglycans heparin and heparan sulfate are endogenous inhibitors of SMC proliferation, yet are able to promote endothelial cell growth (Castellot, J. J. Jr.; Wright, T. C.; Karnovsky, M. J. *Seminars in Thrombosis and Hemostasis* 1987, 13, 489). However, the full clinical benefits of heparin, heparin fragments, chemically modified heparin, low molecular weight heparins, and other heparin mimicking anionic polysaccharides may be compromised due to other pharmacological liabilities (excessive bleeding arising from anticoagulation effects, in particular) coupled with heterogeneity of the various preparations (Borman, S. *Chemical and Engineering News*, Jun. 28, 27, 1993).

WO 96/14325 discloses acylated benzylglycosides as smooth muscle cell proliferation inhibitors. The compounds of the present invention differ in that (a) the carbohydrate moiety is maltotriose and (b) the substituents on the carbohydrate backbone are substantially different.

Zehavi, U., in *Carbohyd. Res.* 1986, 151, 371, disclosed 4-carboxy-2-nitrobenzyl 4-O-α-D-glucopyranosyl-β-D-glucopyranoside which is attached to a polymer for study as an acceptor in the glycogen synthase reaction. The compounds of the present invention differ in that (a) the carbohydrate moiety is maltotriose, (b) the substituents on the benzyl groups are different and (c) the use (smooth muscle antiproliferation) is different.

Patent numbers U.S. Pat. No. 5,498,775, WO96/14324, and U.S. Pat. No. 5,464,827 describe polyanionic benzylglycosides or cyclodextrins as smooth muscle cell proliferation inhibitors for treating diseases and conditions which are characterized by excessive smooth muscle proliferation. β-cyclodextrin tetradecasulfate has been described as a smooth muscle cell proliferation inhibitor and as an effective inhibitor of restenosis (Reilly, C. F.; Fujita, T.; McFall, R. C.; Stabilito, I. I.; Wai-se E.; Johnson, R. G. *Drug Development Research* 1993, 29, 137). U.S. Pat. No. 5,019,562 discloses anionic derivatives of cyclodextrins for treating pathological conditions associated with undesirable cell or tissue growth. WO 93/09790 discloses antiproliferative polyanionic derivatives of cyclodextrins bearing at least 2 anionic residues per carbohydrate residues. Meinetsberger (EP 312087 A2 and EP 312086 A2) describes the antithrombotic and anticoagulant properties of sulfated bis-aldonic acid amides. U.S. Pat. No. 4,431,637 discloses polysulfated phenolic glycosides as modulators of the complement system. The compounds of the present invention differ from all of the prior art in that the compounds (a) are benzylmaltotriosides which bear no structural resemblance to heparin, sulfated cyclodextrins, or to sulfated lactobionic acid dimers, (b) contain no more than three contiguous sugar residues (trisaccharide) and (c) are of a defined structure.

DESCRIPTION OF THE INVENTION

This invention provides benzylmaltotriosides of formula I

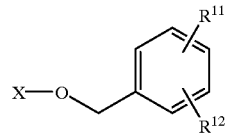

wherein X is

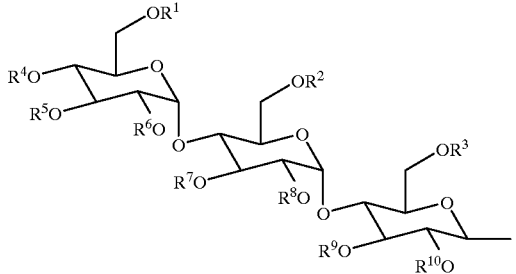

$R^1$, $R^2$, $R^3$, $R^4$, $R^5$, $R^6$, $R^7$, $R^8$, $R^9$ and $R^{10}$, are each, independently, hydrogen, acyl of 2–7 carbon atoms, perfluoroacyl of 2–10 carbon atoms, alkyl of 1–6 carbon atoms, perfluoroalkyl of 1–6 carbon atoms, benzoyl, benzyl or —SO$_3$M;

M is hydrogen, lithium, sodium, potassium or ammonium;

$R^{11}$ is hydrogen, alkyl of 1–6 carbon atoms, perfluoroalkyl of 1–6 carbon atoms, halogen, nitrile, nitro, or alkoxy of 1–6 carbon atoms;

$R^{12}$ is hydrogen, nitro, amino, acylamino of 2–7 carbon atoms, perfluoroacylamino of 2–7 carbon atoms, alkylamino of 1–6 carbon atoms, perfluoroalkylamino of 1–6 carbon atoms, dialklylamino where each alkyl chain is independently 1–6 carbon atoms, perfluorodialklylamino where each alkyl chain is independently 1–6 carbon atoms alkylsulfonylamino of 1–6 carbon atoms, perfluoroalkylsulfonylamino of 1–6 carbon atoms, arylsulfonylamino of 6–10 carbon atoms or arylsulfonylamino substituted with halo of 6–10 carbon atoms;

or a pharmaceutically acceptable salt thereof.

Alkyl, alkoxy, alkylsulfonylamino, acylamino and acyl includes both straight chain as well as branched moieties optionally substituted with fluorine. Halogen means bromine, chlorine, fluorine, and iodine. Aryl is defined as a fully unsaturated carbocyclic radical containing one or more rings having 6–10 carbon atoms optionally substituted with fluorine; with phenyl and naphthyl radicals being preferred.

Pharmaceutically acceptable salts can be formed from organic and inorganic acids, for example, acetic, propionic, lactic, citric, tartaric, succinic, fumaric, maleic, malonic, mandelic, malic, phthalic, hydrochloric, hydrobromic, phosphoric, nitric, sulfuric, methanesulfonic, napthalenesulfonic, benzenesulfonic, toluenesulfonic, camphorsulfonic, and similarly known acceptable acids. Salts may also be formed from organic and inorganic bases, preferably alkali metal salts, for example, sodium, lithium, or potassium. Acid addition salts can be prepared when the compound of formula I contains a basic nitrogen, and base addition salts can typically be prepared when the compound of formula I contains a hydroxyl group.

The compounds of this invention may contain an asymmetric carbon atom and some of the compounds of this invention may contain one or more asymmetric centers and may thus give rise to optical isomers and diastereomers. While shown without respect to stereochemistry in Formula I, the present invention includes such optical isomers and diastereomers; as well as the racemic and resolved, enantiomerically pure R and S stereoisomers; as well as other mixtures of the R and S stereoisomers and pharmaceutically acceptable salts thereof.

Preferred compounds of this invention are benzylmaltosides of formula I

I

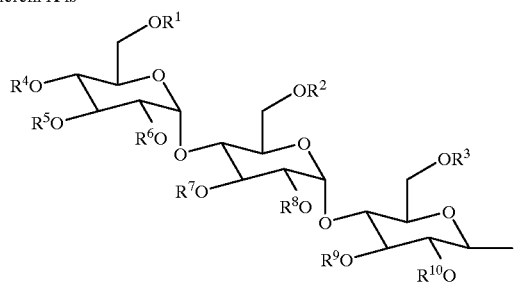

wherein X is $R^1$, $R^2$, $R^3$, $R^4$, $R^5$, $R^6$, $R^7$, $R^8$, $R^9$ and $R^{10}$, are each, independently, hydrogen, acyl of 2–7 carbon atoms, or —$SO_3M$;

M is lithium, sodium, potassium or ammonium;

$R^{11}$ is halogen;

$R^{12}$ is nitro, amino, or acylamino of 2–7 carbon atoms;

or a pharmaceutically acceptable salt thereof.

More preferred compounds of this invention are benzyl-maltosides of formula I

I

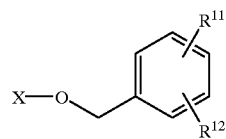

wherein X is

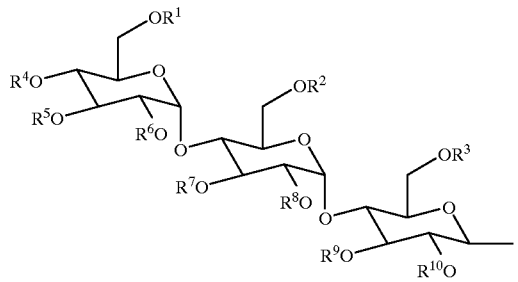

$R^1$, $R^2$, $R^3$, $R^4$, $R^5$, $R^6$, $R^7$, $R^8$, $R^9$ and $R^{10}$, are each, independently, hydrogen, acetyl, or —$SO_3M$;

M is lithium, sodium, potassium or ammonium;

$R^{11}$ is chloro;

$R^{12}$ is hydrogen, nitro, amino, or acetylamino;

or a pharmaceutically acceptable salt thereof.

Specifically preferred compounds of this invention are:

5-(Deca-O-acetyl-β-D-maltotriosyloxymethyl)-2-chloro-1-nitrobenzene or a pharmaceutically acceptable salt thereof;

N-[5-(Deca-O-acetyl-β-D-maltotriosyloxymethyl)-2-chloro-phenyl]-acetamide or a pharmaceutically acceptable salt thereof;

N-[5-(β-D-maltotriosyloxymethyl)-2-chloro-phenyl]-acetamide or a pharmaceutically acceptable salt thereof;

N-[5-(Deca-O-sulfo-β-D-maltotriosyloxymethyl)-2-chloro-phenyl]-acetamide decasodium salt or a pharmaceutically acceptable salt thereof; and 5-(β-D-maltotriosyloxymethyl)-2-chloro-phenylamine or a pharmaceutically acceptable salt thereof.

The compounds of this invention were be prepared according to the following schemes from commercially available starting materials or starting materials which can be prepared using literature procedures. This scheme shows the preparation of representative compounds of this invention.

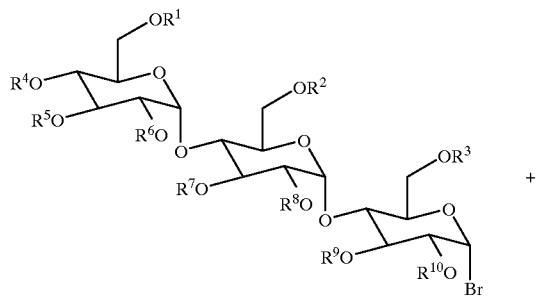

1

+

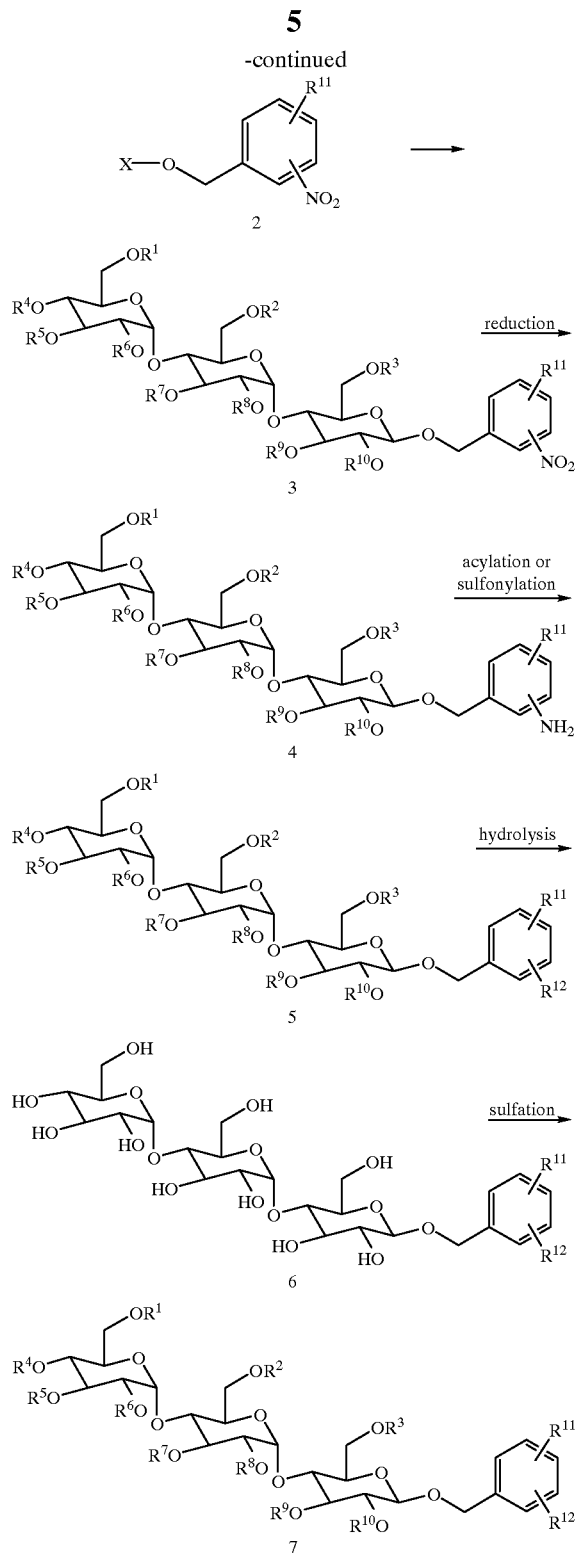

where $R^1$, $R^2$, R4, $R^5$, $R^6$, $R^7$, $R^8$, $R^9$, $R^{10}$, $R^{11}$ and $R^{12}$ are as defined above.

Thus, maltotriosyl bromide 1 is coupled with a benzyl alcohol 2 in the presence of a catalyst such as a mercuric bromide, mercuric cyanide, silver triflate or silver perchlorate in an aprotic solvent such as acetonitrile, dichloromethane, ether, toluene or nitromethane at temperatures ranging from −40° C. to reflux to yield glycoside 3. Reduction of the nitro group of 3 can be accomplished with a reducing agent such as stannous chloride in a polar aprotic solvent such as such as ethyl acetate at ambient temperature to reflux or by catalytic hydrogenation in the presence of a catalyst such as palladium on carbon gives an anilino compound 4. Coupling of 4 with an acid chloride or a sulfonyl chloride can be completed in the presence of an amine base such as triethylamine, diisopropylethylamine or pyridine in an aprotic solvent such as dichloromethane or tetrahydrofuran at temperatures ranging from −20° C. to ambient temperature gives the amide 5. The acetate groups of 5 can be replaced by hydrolysis with a base such as sodium methoxide in methanol or aqueous sodium hydroxide in methanol at ambient temperature to reflux to yield 6. Sulfation of some or all of the free hydroxyl groups on the sugars with a reagent such as sulfur trioxide-trimethylamine complex or sulfur trioxide-pyridine complex in a polar aprotic solvent such as dimethylformamide or dimethylsulfoxide at temperatures ranging from 0° C. to 100° C. to give compound 7.

The compounds of this invention are useful as antiproliferative agents. The following procedures show the evaluation of representative compounds of this invention in standard pharmacological test procedure which measured ability of the evaluated compound to inhibit smooth muscle cell proliferation.

Effects of Compounds on Cell Proliferation Using $^3$H Thymidine Incorporation

Human and porcine smooth muscle cells were tested in early passage (generally passage 3–7) at sub-confluent conditions. Cultures were grown in 16 mm (24 well) multi-well culture dishes in medium 199 supplemented with 10% fetal bovine serum and 2% antibiotic/antimycotic. At sub-confluence, the cells were placed in a defined serum free medium (AIM-V; Gibco) for 24–48 h prior to initiating the experimental protocol.

Although compounds were found to be more effective with longer pre-incubations, in general, the procedures were initiated with the addition of compound, $^3$H thymidine and serum/growth factor to serum deprived synchronized cells and results are reported accordingly.

Compounds were added to each well at 50 fold dilution (20 μL/well) and the plates were incubated for 24–36 h at 37° C. in 5% $CO_2$. Compounds were initially dissolved in 50% ethanol and serially diluted into media. Compounds were routinely evaluated at concentrations from 1 to 100 μM. As a control, grade II porcine intestinal mucosal heparin (sodium salt) was routinely evaluated in all cell preparations at concentrations from 0.1 to 100 μg/mL.

At the completion of the test procedure, plates were placed on ice, washed three times with ice cold phosphate buffered saline (PBS) and incubated in ice cold 10% trichloroacetic acid (TCA) got 30 min to remove acid soluble proteins. Solution was transferred to scintillation vials containing 0.4 N HCl (500 μL/vial to neutralize NaOH) and each well was rinsed two times with water (500 μL) for a total volume of 2 mL/vial.

Data was obtained, in triplicate, for both control and experimental samples. Control (100%) data was obtained from maximally stimulated cells, as the result of growth factor or serum stimulation. Experimental data was obtained from cells maximally stimulated with growth factor or serum and treated with compound. Data are expressed as an $IC_{50}$ in Table I below.

TABLE 1

| Compound of Example | Porcine Smooth Muscle Cell Antiproliferation IC50 |
| --- | --- |
| 1 | 1.8 $\mu$M |
| 2 | 22.5 $\mu$M |
| 3 | 10% inhibition @ 500 $\mu$M |
| 4 | 111.7 $\mu$M |
| 5 | 25% inhibition @ 500 $\mu$M |

The compounds of this invention are useful in treating or inhibiting diseases which are characterized by excessive smooth muscle cell proliferation (smooth muscle cell hyperproliferation). The compounds are particularly useful in treating hyperproliferative vascular diseases which are characterized by smooth muscle cell hyperproliferation, such as restenosis, which most frequently arises from vascular reconstructive surgery and transplantation, for example, balloon angioplasty, vascular graft surgery, coronary artery bypass surgery, and heart transplantation. Other disease states in which there is unwanted "cellular" vascular proliferation include hypertension, asthma, and congestive heart failure. The compounds of this invention are also useful as inhibitors of angiogenesis. Angiogenesis (neovascularization), the process by which new capillaries are formed, is of principal importance for a number of pathological events including chronic inflammation and malignant processes. The compounds of this invention are therefore useful as antineoplastic agents.

The compounds of this invention can be formulated neat or with a pharmaceutical carrier for administration, the proportion of which is determined by the solubility and chemical nature of the compound, chosen route of administration and standard pharmacological practice. The pharmaceutical carrier may be solid or liquid.

A solid carrier can include one or more substances which may also act as flavoring agents, lubricants, solubilizers, suspending agents, fillers, glidants, compression aids, binders or tablet-disintegrating agents; it can also be an encapsulating material. In powders, the carrier is a finely divided solid which is in admixture with the finely divided active ingredient. In tablets, the active ingredient is mixed with a carrier having the necessary compression properties in suitable proportions and compacted in the shape and size desired. The powders and tablets preferably contain up to 99% of the active ingredient. Suitable solid carriers include, for example, calcium phosphate, magnesium stearate, talc, sugars, lactose, dextrin, starch, gelatin, cellulose, methyl cellulose, sodium carboxymethyl cellulose, polyvinylpyrrolidine, low melting waxes and ion exchange resins.

Liquid carriers are used in preparing solutions, suspensions, emulsions, syrups, elixirs and pressurized compositions. The active ingredient can be dissolved or suspended in a pharmaceutically acceptable liquid carrier such as water, an organic solvent, a mixture of both or pharmaceutically acceptable oils or fats. The liquid carrier can contain other suitable pharmaceutical additives such as solubilizers, emulsifiers, buffers, preservatives, sweeteners, flavoring agents, suspending agents, thickening agents, colors, viscosity regulators, stabilizers or osmo-regulators. Suitable examples of liquid carriers for oral and parenteral administration include water (partially containing additives as above, e.g. cellulose derivatives, preferably sodium carboxymethyl cellulose solution), alcohols (including monohydric alcohols and polyhydric alcohols, e.g. glycols) and their derivatives, lethicins, and oils (e.g. fractionated coconut oil and arachis oil). For parenteral administration, the carrier can also be an oily ester such as ethyl oleate and isopropyl myristate. Sterile liquid carriers are useful in sterile liquid form compositions for parenteral administration. The liquid carrier for pressurized compositions can be halogenated hydrocarbon or other pharmaceutically acceptable propellant.

Liquid pharmaceutical compositions which are sterile solutions or suspensions can be utilized by, for example, intramuscular, intraperitoneal or subcutaneous injection. Sterile solutions can also be administered intravenously. The compounds of this invention can also be administered orally either in liquid or solid composition form.

The compounds of this invention may be administered rectally or vaginally in the form of a conventional suppository. For administration by intranasal or intrabronchial inhalation or insufflation, the compounds of this invention may be formulated into an aqueous or partially aqueous solution, which can then be utilized in the form of an aerosol. The compounds of this invention may also be administered transdermally through the use of a transdermal patch containing the active compound and a carrier that is inert to the active compound, is non toxic to the skin, and allows delivery of the agent for systemic absorption into the blood stream via the skin. The carrier may take any number of forms such as creams and ointments, pastes, gels, and occlusive devices. The creams and ointments may be viscous liquid or semisolid emulsions of either the oil-in-water or water-in-oil type. Pastes comprised of absorptive powders dispersed in petroleum or hydrophilic petroleum containing the active ingredient may also be suitable. A variety of occlusive devices may be used to release the active ingredient into the blood stream such as a semipermeable membrane covering a reservoir containing the active ingredient with or without a carrier, or a matrix containing the active ingredient. Other occlusive devices are known in the literature.

The dosage requirements vary with the particular compositions employed, the route of administration, the severity of the symptoms presented and the particular subject being treated. Based on the results obtained in the standard pharmacological test procedures, projected daily dosages of active compound would be 0.1 to 10 mg/kg administered parenterally (intravenous preferred), with projected daily oral dosage being approximately ten-fold higher. Anticipated intravenous administration would last for approximately 5–30 days following acute vascular injury (i.e., balloon angioplasty or transplantation) and for a longer duration for the treatment of chronic disorders. Treatment will generally be initiated with small dosages less than the optimum dose of the compound. Thereafter the dosage is increased until the optimum effect under the circumstances is reached; precise dosages for oral, parenteral, nasal, or intrabronchial administration will be determined by the administering physician based on experience with the individual subject treated. Preferably, the pharmaceutical composition is in unit dosage form, e.g. as tablets or capsules. In such form, the composition is sub-divided in unit dose containing appropriate quantities of the active ingredient; the unit dosage forms can be packaged compositions, for example, packaged powders, vials, ampoules, pre filled syringes or sachets containing liquids. The unit dosage form can be, for example, a capsule or tablet itself, or it can be the appropriate number of any such compositions in package form.

The following provides the preparation of representative compounds of this invention.

EXAMPLE 1

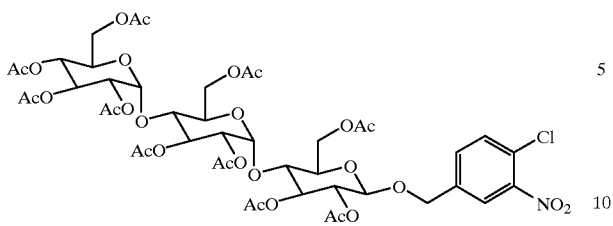

At ambient temperature, to a stirred solution containing 4-chloro-3-nitrobenzyl alcohol (5.48 g, 0.0292 mol), $HgBr_2$ (11.82 g, 0.0321 mol) and $Hg(CN)_2$ (7.45 g, 0.0292 mol) in $CH_3NO_2$ was added acetobromomaltotriose (28.85 g, 0.0292 mol). After 16 h, the reaction was diluted with $CH_2Cl_2$ (500 mL) and filtered through a 1" sulka floc pad, rinsing with $CH_2Cl_2$. The filtrate was washed with brine (3×1 L), dried ($MgSO_4$) and concentrated. Purification on silica gel, eluting with a 0, 1, 2 & 3% MeOH/CHCl3 gradient gave 11.64 g, of the title compound as a white solid, mp 85–100° C.; $^1$H NMR (DMSO-$d_6$) δ 1.931 (s, 3 H), 1.938 (s, 3 H), 1.941, (s, 3 H), 1.944 (s, 3 H), 1.952 (s, 3 H), 1.968 (s, 3 H), 1.975 (s, 3 H), 2.004 (s, 3 H), 2.065 (s, 3 H), 2.076 (s, 3 H), 3.91–4.00 (m, 6 H), 4.12–4.18 (m, 2 H), 4.23 (dd, 1 H), 4.35 (t, 2 H), 4.68–4.99 (m, 7 H), 5.17–5.34 (m, 5 H), 7.59 (dd, 1 H), 7.77 (d, 1 H), 7.95 (s, 1 H). IR (KBr) 2950, 1750, 1375, 1230 and 1050 cm$^{-1}$, mass spectrum (FAB), m/z 1094 (M+H). Anal. Calcd. for $C_{45}H_{56}NClO_{28}$: C, 49.39; H, 5.16; N, 1.28. Found: C, 49.08; H, 5.09; N, 1.27.

EXAMPLE 2

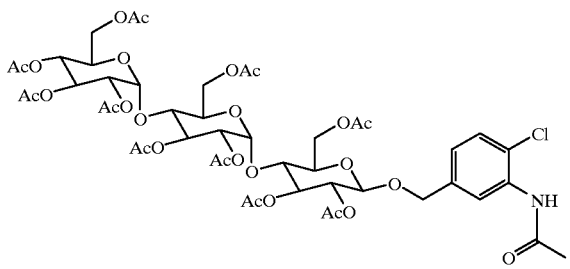

Step 1

5-(Deca-O-acetyl-β-D-maltotriosyloxymethyl)-2-chlorophenylamine

A stirred solution containing 5-(deca-O-acetyl-β-D-maltotriosyloxymethyl)-2-chloro-1-nitrobenzene (2.58 g, 2.36 mmol) and tin (II) chloride dihydrate 3.73 g, 16.5 mmol) in EtOAc (47 mL) was refluxed for 1.5 h. The reaction was cooled to ambient temperature, carefully quenched with saturated aqueous $NaHCO_3$ (50 mL), diluted with EtOAc (50 mL), stirred for 0.5 h and filtered. The biphasic filtrate was separated and the aqueous layer extracted with EtOAc. The combined organic extracts were dried ($K_2CO_3$) and concentrated. Purification on silica gel, eluting with a 0, 1 & 2% MeOH/CHCl3 gradient gave 2.37 g (94%) of the title compound as a white solid, mp 85–100° C.; $^1$H NMR (DMSO-$d_6$) δ 1.922 (s, 3 H), 1.935 (s, 3 H), 1.937 (s, 3 H), 1.942 (s, 3 H), 1.946 (s, 3 H), 1.969 (s, 3 H), 1.977 (s, 3 H), 2.007 (s, 3 H), 2.070 (s, 3 H), 2.094 (s, 3 H), 3.88–4.01 (m, 6 H), 4.13–4.18 (m, 2 H), 4.24–4.28 (m, 1 H), 4.32–4.39 (m, 3 H), 4.59 (d, 1 H), 4.67–4.86 (m, 4 H), 4.97 (t, 1 H), 5.17–5.38 (m, 7 H), 6.43 (dd, 1 H), 6.67 (d, 1 H), 7.13 (d, 1 H). IR (KBr) 3475, 3375, 2950, 1750, 1230 and 1040 cm$^{-1}$, mass spectrum (FAB), m/z 1064 (M+H).

Step 2

N-[5-(Deca-O-acetyl-β-D-maltotriosyloxymethyl)-2-chloro-phenyl]-acetamide

At ambient temperature, to a stirred solution containing 5-(deca-O-acetyl-β-D-maltotriosyloxymethyl)-2-chlorophenylamine (1.62 g, 1.52 mmol) and triethylamine (1.72 mL, 12.3 mmol) in THF (15 mL) was added acetyl chloride (0.294 mL, 4.12 mmol). After 4 days, the reaction was quenched with saturated aqueous $NaHCO_3$ (40 mL), diluted with brine (30 mL) and extracted with EtOAc. The combined organic extracts were dried ($K_2CO_3$) and concentrated. Purification on silica gel, eluting with a 1, 2 & 3% MeOH/CHCl3 gradient, followed by a second chromatography eluting with 50% acetone/hexane gave 0.353 g of the title compound as a pale yellow solid, mp 93–100° C.; $^1$H NMR (DMSO-$d_6$) δ 1.92–2.01 (m, 24 H), 2.07 (s, 6 H), 2.09 (s, 3 H), 3.89–4.01 (m, 6 H), 4.13–4.18 (m, 2 H), 4.24–4.28 (m, 2 H), 4.32–4.35 (m, 2 H), 4.53 (d, 1 H), 4.69–4.77 (m, 3 H), 4.83–4.86 (m, 2 H), 4.97 (t, 1 H), 5.17–5.33 (m, 5 H), 7.07 (dd, 1 H), 7.45 (d, 1 H), 7.62 (s, 1 H), 9.51 (s, 1 H). IR (KBr) 3425, 1760, 1230 and 1050 cm$^{-1}$, mass spectrum (FAB), m/z 1106 (M+H). Anal. Calcd. for $C_{47}H_{60}NClO_{27}$: C, 51.02; H, 5.47; N, 1.27. Found: C, 50.92; H, 5.36; N, 1.38.

EXAMPLE 3

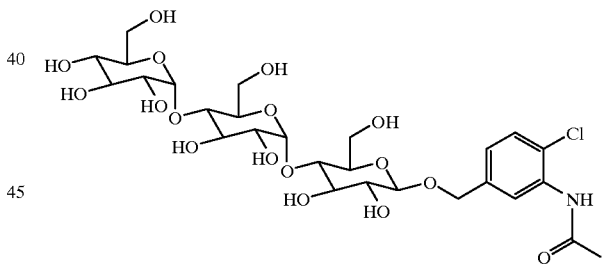

A stirred solution containing N-[5-(deca-O-acetyl-β-D-maltotriosyloxymethyl)-2-chloro-phenyl]-acetamide (1.032 g, 0.933 mmol) and 25 weight % NaOMe in MeOH (0.101 g, 0.467 mmol) in MeOH (30 mL) was refluxed for 4.5 h. The reaction was cooled to ambient temperature and concentrated. Purification on Dynamax C18, eluting with 15% $CH_3CN/H_2O$ gave 0.428 g (67%) of the title compound as a white solid, mp 135–148° C.; $^1$H NMR (DMSO-$d_6$) δ 2.07 (s, 3 H), 3.02–3.11 (m, 2 H), 3.20–3.49 (m, 9 H) 3.53–3.66 (m, 6 H), 3.69–3.73 (m, 1 H), 4.27 (d, 1 H), 4.49–4.57 (m, 4 H), 4.80 (d, 1 H), 4.85–4.87 (m, 2 H), 4.98 (d, 1 H), 5.02 (d, 1 H), 5.24 (d, 1 H), 5.45 (br. s, 2 H), 5.52 (br. s, 2 H), 7.21 (dd, 1 H), 7.44 (d, 1 H), 7.64 (s, 1 H), 9.52 (s, 1 H). IR (KBr) 3400, 2900, 1675 and 1030 cm$^{-1}$, mass spectrum (FAB), m/z 686 (M+H). Anal. Calcd. for $C_{27}H_{40}NClO_{17}\cdot H_2O$: C, 46.06; H, 6.01; N, 1.99. Found: C, 46.07; H, 6.09; N, 1.99.

EXAMPLE 4

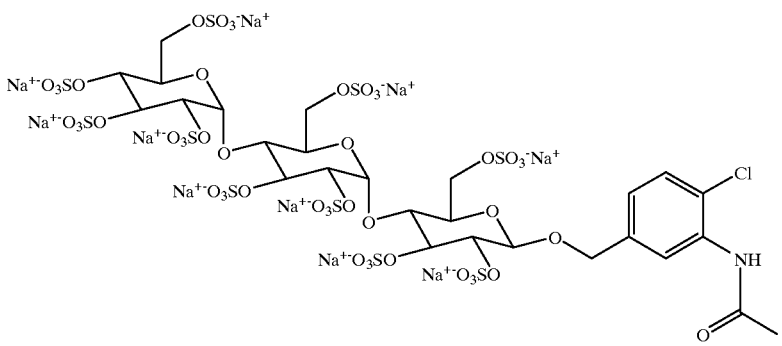

A stirred solution containing 5-(β-D-maltotriosyloxymethyl)-2-chlorophenylamine (0.278 g, 4.05 mmol) and sulfur trioxide-trimethylamine complex (2.82 g, 20.3 mmol) in DMF (20 mL) was stirred at 70° C. for 48 h. The reaction was cooled to ambient temperature, diluted with $H_2O$ (50 mL), filtered and the filtrate concentrated. Purification on Sephadex G-10, eluting with $H_2O$ followed by cation ion exchange on Dowex 50×8 strongly acidic resin (Na form) gave 0.596 g (86%) of the title compound as a white solid, mp 173° C.; $^1$H NMR ($H_2O$-$d_2$) δ 2.09 (s, 3 H), 3.93–4.28 (m, 11 H), 4.38–4.48 (m, 2 H), 4.49–4.57 (m, 2 H), 4.60–4.69 (m, 2 H), 4.76–4.85 (m, 4 H), 5.40 (d, 1 H), 5.50 (d, 1 H), 7.29 (dd, 1 H), 7.41–7.44 (m, 2 H). IR (KBr) 3450, 2950, 1650 and 1250 $cm^{-1}$, mass spectrum (FAB), m/z 1681 (M−H). Anal. Calcd. for $C_{27}H_{30}NClO_{47}Na_{10}6.H_2O$: C, 17.87; H, 2.33; N, 0.77. Found: C, 17.84; H, 2.41; N, 0.78.

EXAMPLE 5

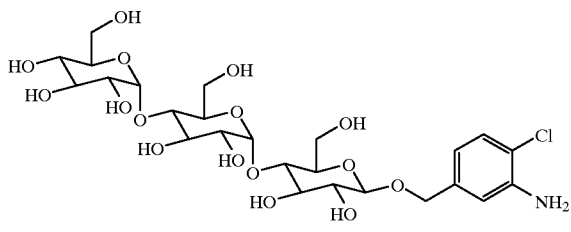

Using 5-(Deca-O-acetyl-β-D-maltotriosyloxymethyl)-2-chlorophenylamine, the title compound was prepared by the procedure of Example 3 to give 0.225 g (75%) of a white solid, mp 95–134° C.; $^1$H NMR ($H_2O$-$d_2$) δ 3.16–3.21 (m, 1 H), 3.27 (t, 1 H), 3.39–3.82 (m, 16 H), 4.36 (d, 1 H), 4.51 (d, 1 H), 4.67 (d, 1 H), 5.24 (t, 1 H), 6.71 (dd, 1 H), 6.85 (d, 1 H), 7.20 (d, 1 H). IR (KBr) 3400, 2900, 1625 and 1025 $cm^{-1}$, mass spectrum (FAB), m/z 644 (M+H). Anal. Calcd. for $C_{25}H_{38}NClO_{16}·H_2O$: C, 45.36; H, 6.09; N, 2.12. Found: C, 45.37; H, 6.34; N, 2.05.

What is claimed is:

1. A method of treating or inhibiting hyperproliferative vascular disorders in a mammal in need thereof, which comprises administering to said mammal an effective amount of a compound of formula I having the structure

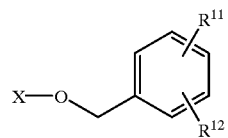

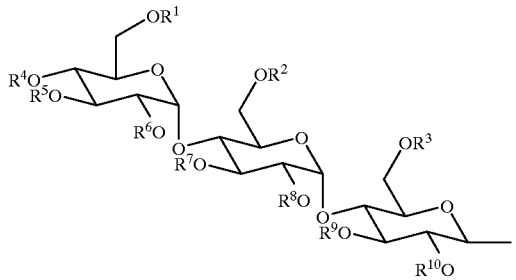

wherein
X is $R^1$, $R^2$, $R^3$, $R^4$, $R^5$, $R^6$, $R^7$, $R^8$, $R^9$ and $R^{10}$, are each, independently, hydrogen, acyl of 2–7 carbon atoms, perfluoroacyl of 2–10 carbon atoms, alkyl of 1–6 carbon atoms, perfluoroalkyl of 1–6 carbon atoms, benzoyl, benzyl or —$SO_3M$;

M is hydrogen, lithium, sodium, potassium or ammonium;

$R^{11}$ is hydrogen, alkyl of 1–6 carbon atoms, perfluoroalkyl of 1–6 carbon atoms, halogen, nitrile, nitro, or alkoxy of 1–6 carbon atoms;

$R^{12}$ is hydrogen, nitro, amino, acylamino of 2–7 carbon atoms, perfluoroacylamino of 2–7 carbon atoms, alkylamino of 1–6 carbon atoms, perfluoroalkylamino of 1–6 carbon atoms, dialklylamino where each alkyl chain is independently 1–6 carbon atoms, perfluorodialklylamino where each alkyl chain is independently 1–6 carbon atoms alkylsulfonylamino of 1–6 carbon atoms, perfluoroalkylsulfonylamino of 1–6 carbon atoms, arylsulfonylamino of 6–10 carbon atoms or arylsulfonylamino substituted with halo of 6–10 carbon atoms;

or a pharmaceutically acceptable salt thereof.

2. A method of treating or inhibiting restenosis in a mammal in need thereof, which comprises administering to said mammal an effective amount of a compound of formula I having the structure

I

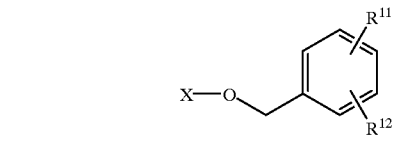

wherein
X is

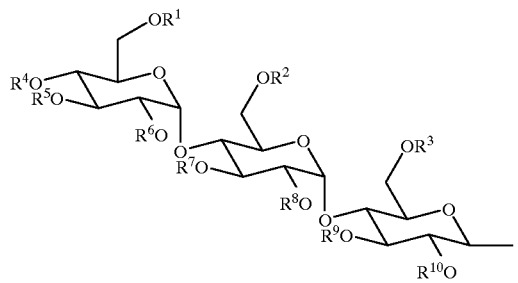

$R^1$, $R^2$, $R^3$, $R^4$, $R^5$, $R^6$, $R^7$, $R^8$, $R^9$ and $R^{10}$, are each, independently, hydrogen, acyl of 2–7 carbon atoms, perfluoroacyl of 2–10 carbon atoms, alkyl of 1–6 carbon atoms, perfluoroalkyl of 1–6 carbon atoms, benzoyl, benzyl or —$SO_3M$;

M is hydrogen, lithium, sodium, potassium or ammonium;

$R^{11}$ is hydrogen, alkyl of 1–6 carbon atoms, perfluoroalkyl of 1–6 carbon atoms, halogen, nitrile, nitro, or alkoxy of 1–6 carbon atoms;

$R^{12}$ is hydrogen, nitro, amino, acylamino of 2–7 carbon atoms, perfluoroacylamino of 2–7 carbon atoms, alkylamino of 1–6 carbon atoms, perfluoroalkylamino of 1–6 carbon atoms, dialklylamino where each alkyl chain is independently 1–6 carbon atoms, perfluorodialklylamino where each alkyl chain is independently 1–6 carbon atoms alkylsulfonylamino of 1–6 carbon atoms, perfluoroalkylsulfonylamino of 1–6 carbon atoms, arylsulfonylamino of 6–10 carbon atoms or arylsulfonylamino substituted with halo of 6–10 carbon atoms;

or a pharmaceutically acceptable salt thereof.

3. The method according to claim 2, wherein the restenosis results from a vascular angioplasty procedure, vascular reconstructive surgery, or organ or tissue transplantation.

4. A method of inhibiting angiogenesis in a malignant tumor, sarcoma, or neoplastic tissue in a mammal in need thereof, which comprises administering to said mammal an effective amount of a compound of formula I having the structure

I

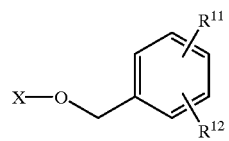

wherein
X is

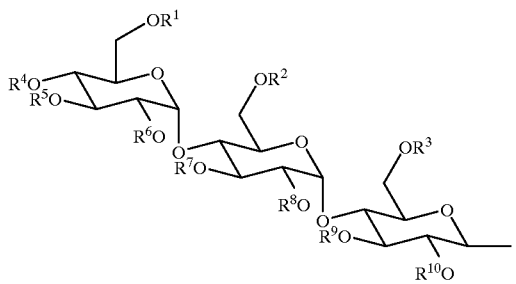

$R^1$, $R^2$, $R^3$, $R^4$, $R^5$, $R^6$, $R^7$, $R^8$, $R^9$ and $R^{10}$, are each, independently, hydrogen, acyl of 2–7 carbon atoms, perfluoroacyl of 2–10 carbon atoms, alkyl of 1–6 carbon atoms, perfluoroalkyl of 1–6 carbon atoms, benzoyl, benzyl or —$SO_3M$;

M is hydrogen, lithium, sodium, potassium or ammonium;

$R^{11}$ is hydrogen, alkyl of 1–6 carbon atoms, perfluoroalkyl of 1–6 carbon atoms, halogen, nitrile, nitro, or alkoxy of 1–6 carbon atoms;

$R^{12}$ is hydrogen, nitro, amino, acylamino of 2–7 carbon atoms, perfluoroacylamino of 2–7 carbon atoms, alkylamino of 1–6 carbon atoms, perfluoroalkylamino of 1–6 carbon atoms, dialklylamino where each alkyl chain is independently 1–6 carbon atoms, perfluorodialklylamino where each alkyl chain is independently 1–6 carbon atoms alkylsulfonylamino of 1–6 carbon atoms, perfluoroalkylsulfonylamino of 1–6 carbon atoms, arylsulfonylamino of 6–10 carbon atoms or arylsulfonylamino substituted with halo of 6–10 carbon atoms;

or a pharmaceutically acceptable salt thereof.

* * * * *